(12) United States Patent
Rothweiler et al.

(10) Patent No.: US 10,793,726 B2
(45) Date of Patent: Oct. 6, 2020

(54) COATING FOR APPLICATORS IN ELECTROSURGERY

(71) Applicant: Aesculap AG, Tuttlingen (DE)

(72) Inventors: Christoph Rothweiler, Donaueschingen (DE); Holger Reinecke, Emmendingen (DE); Dieter Weißhaupt, Immendingen (DE)

(73) Assignee: AESCULAP AG, Tuttlingen (DE)

( * ) Notice: Subject to any disclaimer, the term of this patent is extended or adjusted under 35 U.S.C. 154(b) by 622 days.

(21) Appl. No.: 15/510,018

(22) PCT Filed: Jun. 30, 2016

(86) PCT No.: PCT/EP2016/065272
§ 371 (c)(1),
(2) Date: Mar. 9, 2017

(87) PCT Pub. No.: WO2017/001548
PCT Pub. Date: Jan. 5, 2017

(65) Prior Publication Data
US 2018/0187027 A1    Jul. 5, 2018

(30) Foreign Application Priority Data
Jul. 2, 2015  (DE) .................. 10 2015 212 389

(51) Int. Cl.
| | | |
|---|---|---|
| *C09D 5/44* | (2006.01) | |
| *A61B 18/14* | (2006.01) | |
| *C09D 127/12* | (2006.01) | |
| *C25D 13/12* | (2006.01) | |
| *C25D 13/20* | (2006.01) | |
| *C25D 15/00* | (2006.01) | |
| *C09D 127/18* | (2006.01) | |
| *C09D 171/00* | (2006.01) | |
| *C09D 177/00* | (2006.01) | |
| *C25D 13/04* | (2006.01) | |
| *C25D 13/06* | (2006.01) | |
| *C25D 13/22* | (2006.01) | |
| *A61B 18/00* | (2006.01) | |

(52) U.S. Cl.
CPC ........ *C09D 5/4461* (2013.01); *A61B 18/1442* (2013.01); *C09D 5/4407* (2013.01); *C09D 5/4419* (2013.01); *C09D 5/4423* (2013.01); *C09D 127/12* (2013.01); *C09D 127/18* (2013.01); *C09D 171/00* (2013.01); *C09D 177/00* (2013.01); *C25D 13/04* (2013.01); *C25D 13/12* (2013.01); *C25D 13/20* (2013.01); *C25D 15/00* (2013.01); *A61B 2018/00136* (2013.01); *A61B 2018/146* (2013.01); *A61B 2018/1462* (2013.01); *C25D 13/06* (2013.01); *C25D 13/22* (2013.01)

(58) Field of Classification Search
CPC .. C09D 5/4461; C09D 5/4407; C09D 5/4419; C09D 5/4423; C09D 127/12; C09D 127/18; C09D 171/00; C09D 177/00; A61B 18/1442; A61B 2018/00136; A61B 2018/146; A61B 2018/1462; A61B 18/1445; A61B 17/07207; A61B 2018/1412; A61B 2018/1455; A61B 17/068; A61B 2017/320052; A61B 18/00107; A61B 2018/00083; C25D 13/04; C25D 13/12; C25D 13/20; C25D 15/00; C25D 13/06; C25D 13/22; H01G 4/32; H01G 4/005; H01G 4/14; H01G 4/18; Y10T 29/435; H01M 4/0457; H01M 4/622; H01M 4/623; H01M 4/386; H01M 4/583; H01M 4/134; H01M 4/133
See application file for complete search history.

(56) References Cited

U.S. PATENT DOCUMENTS

| | | |
|---|---|---|
| 3,434,942 A * | 3/1969 | Waterman ............... F16C 33/04 205/224 |
| 3,450,655 A | 6/1969 | Spiller et al. |
| 5,415,750 A | 5/1995 | Klein et al. |
| 5,846,237 A | 12/1998 | Nettekoven |
| 9,066,723 B2 | 6/2015 | Beller et al. |
| 2003/0139741 A1 | 7/2003 | Goble et al. |
| 2004/0238371 A1 | 12/2004 | Franz |
| 2008/0077131 A1 | 3/2008 | Yates et al. |
| 2012/0211365 A1 | 8/2012 | Joung et al. |

FOREIGN PATENT DOCUMENTS

| | | |
|---|---|---|
| DE | 1916179 | 10/1969 |
| WO | 2014170011 | 10/2014 |

OTHER PUBLICATIONS

Corni et al., "Polyetheretherketone (PEEK) Coatings on Stainless Steel by Electrophoretic Deposition." Advanced Engineering Materials (2008) 10(6):559-564.

* cited by examiner

*Primary Examiner* — Xiuyu Tai
(74) *Attorney, Agent, or Firm* — Lewis Kohn & Walker LLP; David M. Kohn

(57) ABSTRACT

A method of applying at least one coating of at least one electrically insulating polymer to an applicator for currents, especially HF currents in surgery, the coating is produced by electrophoretic deposition from a suspension of the polymer in at least one organic solvent, wherein the applicators thus coated are especially clamps, pairs of tweezers or pairs of scissors which are used in the bipolar application technique of HF surgery. Polymers used are especially thermoplastic polymers, such as thermoplastic fluoropolymers, and more particularly polychlorotrifluoroethylene (PCTFE) or ethylene chlorotrifluoroethylene (ECTFE).

15 Claims, No Drawings

COATING FOR APPLICATORS IN ELECTROSURGERY

This application is a United States National Stage Application claiming the benefit of priority under 35 U.S.C. 371 from International Patent Application No. PCT/EP2016/065272 filed Jun. 30, 2016, which claims the benefit of priority from German Patent Application Serial No. DE 102015212389.8 filed Jul. 2, 2015, the entire contents of which are herein incorporated by reference.

The invention relates firstly to a method of applying at least one coating of at least one electrically insulating polymer to an applicator for currents, especially HF currents in surgery, and to an applicator coated in this way. The invention secondly relates to a suspension for the electrophoretic deposition of at least one coating on an applicator for currents, especially HF currents in surgery.

In what is called electrosurgery (high-frequency surgery, HF surgery), alternating current with high frequency is passed through the human body. The electrical energy of the alternating current is converted here primarily to thermal energy in the body tissue. Depending mainly on the form of what is called the active electrode that forms the surgical instrument, the tissue can be cut by the electrode at high current densities (electrotomy) or coagulated for hemostasis at low current densities.

In what is called the monopolar technique of HF surgery, one pole of the high-frequency voltage source is connected to the patient via a neutral electrode over a maximum area. The other pole of the voltage source is connected to the active electrode that forms the actual surgical instrument.

In what is called the bipolar technique of HF surgery, two mutually insulated electrodes between which the HF voltage is applied are conducted directly to the operation site. The circuit is completed via the tissue between the electrodes, such that the current, by contrast with the monopolar technique, flows only through a small part of the body. The thermal effect caused by the current flow accordingly occurs primarily only in the tissue between the electrodes.

Known monopolar or bipolar instruments for application of high-frequency currents for cutting and/or coagulating tissue in surgery are, for example, pairs of tweezers, clamps, and pairs of scissors or hooks.

In many applications of HF surgery, especially in the case of the bipolar application technique, it is either absolutely necessary or at least advantageous to provide the corresponding instruments or instrument parts that are generally manufactured from metallic and hence electrically conductive materials with an (electrical) insulation. This is generally accomplished with the aid of suitable electrically insulating polymers which are frequently applied as coatings to the corresponding instruments or instrument parts.

A similar topic also exists, inter alia, in the stimulation of nerves by current with the aid of what is called a nerve stimulation needle. In this case, for example, a nerve can be selectively localized and then, if appropriate, even anesthetized (regional anesthesia).

The application of corresponding insulating coatings is currently performable with reproducible results only with difficulty or in a costly and inconvenient manner in many cases according to the current prior art. For instance, electrically insulating polymers are deposited, for example, by electrostatic means or by fluidized sintering methods. In such processes, however, it is frequently not possible to achieve exactly repeatable coating conditions. The introduction of unwanted foreign bodies into the coating can also constitute a problem. Finally, it is frequently impossible by such processes to provide layer thicknesses having particular values for what is called the (electrical) breakdown resistance specifically for the particular electrically insulating polymer. The effect of this is that much thicker insulating polymer layers are currently generally deposited for safety reasons than would actually be necessary according to the product specifications of the particular polymer.

Accordingly, it is an object of the invention to provide an alternative coating method, especially for the coating of applicators for HF surgery with electrically insulating polymers. More particularly, it is to be possible with the aid of this alternative coating method to control the thickness of the particular polymer coating(s) such that particular values for the electrical breakdown resistance are achieved at minimum (optimized) layer thicknesses.

This object is achieved by the method of the invention having the features of applying at least one coating of at least one electrically insulating polymer to an applicator for currents, especially HF currents in surgery, especially to a clamp, to a pair of tweezers or to a pair of scissors, characterized in that the coating is produced at least partly, preferably entirely, by electrophoretic deposition from a suspension of the polymer in at least one organic solvent. Preferred executions of this method are defined in the claims that are dependent on this method claim. Further parts of the invention are the applicator of the invention for currents, especially HF currents in surgery, especially a clamp, pair of tweezers or pair of scissors, having at least one coating of at least one electrically insulating polymer, characterized in that the polymer has been produced by electrophoretic deposition from a suspension of the polymer in at least one organic solvent, and the suspension of the invention for the electrophoretic deposition of at least one coating on an applicator for currents, especially HF currents in surgery, especially to a clamp, to a pair of tweezers or to a pair of scissors, characterized in that the suspension comprises at least one electrically insulating polymer in at least one organic solvent. Preferred executions of the applicator of the invention and the suspension of the invention are defined in the dependent claims in each case.

According to the invention, the process of the type specified at the outset is characterized in that the coating of the electrically insulating polymer is produced at least partly, but preferably entirely, by electrophoretic deposition. This electrophoretic deposition is effected from a suspension of the polymer in at least one organic solvent. More particularly, the coating can also be provided by at least two and preferably several deposition operations/deposition steps.

Electrophoretic deposition (EPD) is a method known from the prior art, in which (electrically) charged particles migrate in an electrical field and are deposited on an electrode. According to the configuration of this method, it is possible to form layers/coatings on a main body which generally serves as the electrode, or to form shaped bodies themselves.

If—as in the present invention—a solid (the electrically insulating polymer here) is to be electrophoretically deposited, it is necessary to bring the polymer particles into suspension in a liquid medium and to provide them with an electrical charge. As is well known, a suspension is a heterogeneous substance mixture of a liquid (the "solvent") and solids finely distributed therein. For provision of the suspension, the solid particles, which are generally at first in the form of powder or granules, are converted to a slurry in the solvent, for example while stirring. There is frequently additional use of dispersants, for example surfactants, which keep the solid particles suspended in the suspension and hinder their sedimentation.

In the present case, the electrophoretic deposition is effected from a suspension of the electrically insulating polymer in at least one organic solvent.

The method of the invention is capable of reliable deposition of an electrically insulating polymer to an applicator for HF currents in surgery by electrophoretic deposition. This is elucidated in more detail hereinafter. What is crucial here is the attainment of a sufficient breakdown resistance (reported in kV/mm). The breakdown resistance is that electrical field strength which is the maximum that can exist in a material (the polymer coating here) without flashover (arcing). The breakdown resistance of an insulating material corresponds to an electrical field strength, and so it can accordingly also be referred to as breakdown field strength.

In connection with the present invention, it is important that the breakdown resistance is not proportional to the thickness in the case of many insulating substances, including electrically insulating polymers. The result of this effect is that, in some cases, thin layers actually have higher breakdown resistances than thick layers. This fact too is elucidated in detail hereinafter in connection with the invention.

In a first group of preferred embodiments of the method of the invention, the polymer applied is a transparent polymer. Accordingly, such a polymer is not visually discernible from the corresponding applicator, i.e. more particularly the (bipolar) clamp or (bipolar) pair of tweezers. As a consequence, the applicator with all its details is apparent to the user even after application of the coating.

In a second group of preferred embodiments of the method of the invention, the electrically insulating polymer used is a colored polymer, this color preferably being provided by the addition of color pigments in the polymer. In this way, the coating is immediately visually discernible from the main body of the applicator, and so coated and uncoated parts of the applicator are distinguishable from one another to the user. Accordingly, such colored polymer coatings can fulfill a distinguishing function for the user, such that, for example, different materials of the applicator or different dimensions, material thicknesses and the like can be identified by different colors.

In principle, according to the invention, a wide variety of different polymers can be used as coating, provided that they satisfy the required properties of an electrical insulation. Preference is given to those polymers which can be provided in a simple manner in the form of particles, i.e. generally in the form of a powder or granules, such that suspensions for electrophoretic deposition are preparable with suitable solvents.

Preference is further given here in an exceptional manner to thermoplastic polymers, i.e. polymers that are (thermoplastically) reversibly deformable within particular temperature ranges. Such simple melting of the electrically insulating polymer may be advantageous in order to optimize the coatings deposited by electrophoresis further in terms of their surface properties by a downstream heat treatment. This too will be elucidated in detail hereinafter.

Preferably, the polymers used in accordance with the invention may be polyamides (PA), the structures and properties of which are well known to the person skilled in the art. Polyamides are predominantly semicrystalline thermoplastics having low electrical conductivity.

Another group of polymers usable with preference is that of the polyaryl ether ketones (PAEKs) containing ether and ketone groups in the polymer chain. These polymers too are well known to the person skilled in the art, and a particularly preferred and known member of this group of polymers is polyether ether ketone (PEEK).

Exceptionally preferred for use in the method of the invention are what are called the fluoropolymers, these being semicrystalline thermoplastics formed from perfluorinated monomers. In these polymers, the hydrogen atoms of the main carbon chains have been wholly or partly replaced by fluorine atoms. Examples of fluoropolymers include polytetrafluoroethylene (PTFE) (although it is not fusible). The fluoropolymers also include the thermoplastic fluoropolymers that are preferred here, which include polyvinylidene fluoride (PVDF).

Among the thermoplastic fluoropolymers, particular preference is given to polychlorotri-fluoroethylene (PCTFE) and ethylene chlorotrifluoro-ethylene (ECTFE). Those polymers are semicrystalline thermoplastic polymers having good strength and hardness which can be converted in the form of powders or granules in suspension for the electrophoretic deposition.

A known ECTFE product is Halar® ECTFE from Solvay Solexis, a 1:1 alternating copolymer of ethylene and chlorotrifluoroethylene.

In a further development, it is preferable in the method of the invention when the application of the polymer coating is preceded by application of what is called a primer layer. Primer layers of this kind, which can also be referred to as adhesion promoter layers or basecoat layers, serve to improve the adhesion of the polymer layer on the surface of the applicator. It is possible here for just one primer layer to be provided, or else what is called a primer system which may consist of two or more layers. The primer layer can be applied by a wide variety of different methods known in the prior art, especially likewise by electrophoretic deposition.

Moreover, it is especially possible to apply at least one coloring layer prior to the application of the polymer coating. This coloring layer can likewise be applied by electrophoretic deposition. In that case, this can be accomplished using a suspension of a color pigment in an organic solvent, especially an alcohol, for example isopropanol, preferably with a surfactant such as sodium dodecylsulfate (SDS). Corresponding pigments are, for example, black dry pigments for PTFE, blue dry pigments for PTFE and nickel titanium yellow dry pigments, as purchasable, for example, from Colorant Chromatics AB, Finland.

The coloring layer can then be coated/overcoated either with a transparent polymer coating or a colored polymer coating by the method of the invention. The coloring layer(s) can preferably likewise be applied with the aid of electrophoretic deposition. This has the advantage that both the coloring layer and the polymer layer (and optionally also the primer layer) can be applied to the applicator with the same apparatus.

In this connection, it is also possible in preferred embodiments to introduce pigments into a primer layer or a primer system, and in this way to produce a coloring effect on the applicator with the aid of these primer layers.

For the production of the corresponding suspensions for the electrophoretic deposition, it is possible in principle to use particles, i.e. polymer particles or pigment particles, of different size. Preference is given here to the use of particles of small size, since it is possible in this way to obtain thinner layers. The after treatment of the layers obtained by subsequent melting, which is described hereinafter, also leads to better results when particles having comparatively small diameters are present in the suspension used for electrophoretic deposition. It is also possible at edges and corners of the applicators to be coated, especially at rounded corners and edges, to better achieve coatings with substantially constant layer thickness when particles having comparatively small diameters are present in the suspensions.

A suitable measure for the distribution of the particle sizes of a polymer material used or of a pigment used is what is called the D50 value, which represents the median particle size. D50 value means that 50% of the particles are smaller than the value reported.

Within the scope of this definition, it is preferable in the method of the invention when the D50 value of the particles used (polymer, primer, pigment) is less than 100 µm, preferably less than 80 µm, especially less than 40 µm. In this connection, it is possible to subject a commercially available product having greater particle size to corresponding processing prior to conversion to the corresponding suspension, for example by at least one grinding operation. It is also possible with the aid of the subsequent processing of an already produced suspension with ultrasound to reduce the diameter of the particles (polymer, primer, pigment) present in the suspension, such that it is possible in this way to achieve lower D50 values of the particles in the suspension.

An example of a suitable test method for determination of particle size is laser diffractometry, as typically used according to the prior art for determination of particle size in suspensions inter alia.

It is further preferable in the method of the invention when the polymer coating obtainable by the method has an electrical breakdown resistance of at least 500 V/mm. Preferably, the electrical breakdown resistance is at least 1200 V/mm, especially at least 2500 V/mm.

In the invention, the polymer coating obtained by the method of the invention preferably has a thickness between 5 µm and 500 µm, preferably of 30 µm to 350 µm. Within the latter range, preference is further given to layer thicknesses of 100 µm to 250 µm.

In addition, in the invention, polymer coatings having layer thicknesses between 5 µm and 100 µm are envisaged, preference further being given to layer thicknesses between 10 µm and 60 µm, especially between 15 µm and 30 µm. Layer thicknesses of this order are especially envisaged in the coating of the nerve stimulation needles mentioned at the outset.

As already elucidated, it is advantageous in the invention when particular desired values for electrical breakdown resistance are achieved at particular, especially minimum, layer thicknesses of the polymer coating. Accordingly, preference is given in the method of the invention to executions in which the electrical breakdown resistance at the above-mentioned layer thicknesses of the polymer coating is between 3 kV/mm and 150 kV/mm, especially between 50 kV/mm and 100 kV/mm.

Especially in such executions of the method of the invention, it is ensured that particular values for electrical breakdown resistance, for example those specified by the manufacturer, at defined layer thicknesses will be made available for each electrically insulating polymer used. This is achieved by the electrophoretic deposition of the polymer particles from a suspension in an organic solvent.

The layer thickness to be applied is determined for each polymer material proceeding from the maximum voltage that the voltage source to be used with the applicator provides. For example, this (maximum) peak voltage Vp may be 600 volts.

In the invention, the electrophoretic deposition of the polymer coating can in principle be effected with any voltage values that are customary in electrophoretic deposition. Preferably, the polymer coating is produced at a voltage between 0.2 kV and 4 kV, especially between 0.5 kV and 2 kV. Within the latter range, preference is further given to voltage values for the electrophoretic deposition between 0.8 kV and 1.2 kV.

The period of time within which the electrophoretic deposition of the polymer coating is effected can also be selected freely in accordance with the invention.

Preference is given here to periods of time between 5 seconds and 10 minutes, with further emphasis for periods of time between 5 seconds and 60 seconds, especially between 10 seconds and 40 seconds.

In a further development, it is preferable in the method of the invention when the electrophoretic deposition is conducted at a temperature between 10° C. and 80° C., especially between 20° C. and 60° C. It is advantageous in principle here when the temperature is kept constant during the electrophoretic deposition in order to assure better reproducibility of the deposition.

In principle, in the invention, it is possible to use different organic solvents or solvent mixtures for production of the corresponding suspension of the polymer particles. An advantageously usable group of organic solvents is that of organic alcohols, especially alkanols, such as ethanol or isopropanol. Preferably, the organic solvents are also aprotic and especially aprotic-nonpolar solvents, especially alkanes. Among these alkanes, emphasis should be given especially to the hexanes and heptanes, preferably n-hexane and n-heptane.

As already mentioned, dispersants, especially surfactants, can be added to the suspension in the method of the invention. Surfactants of this kind are known to those skilled in the art, and sodium dodecylsulfate (SDS) shall be mentioned here merely as an example.

In a further development, it is preferable in the method of the invention when the applicator provided with the polymer coating is dried after the electrophoretic deposition. This drying serves primarily to remove excess organic solvent from the surface of the coating. Such a drying operation is generally effected well below the melting temperature of the corresponding electrically insulating polymer.

In a further development, the polymer coating produced by electrophoretic deposition, in the method of the invention, is subjected to an aftertreatment by melting. This aftertreatment serves to further improve the quality of the polymer coating, especially of the surface of this polymer coating, and can preferably be conducted in the invention after every electrophoretic deposition step. The melting at least partly closes any defects present, such as pores, in the coating and/or at least partly balances out any unevenness present in the coating. Accordingly, reference may also be made here to homogenization of the polymer coating by melting. Transitions with gradually decreasing layer thickness between coated and uncoated regions on the applicator can also be realized efficiently with the aid of the melting. This type of aftertreatment can be conducted in a particularly advantageous manner in the case of thermoplastic polymers as usable in the invention.

In principle, said after treatment is possible at any desired temperatures at which at least softening of the corresponding polymer occurs. Accordingly, this softening temperature forms the lower limit for viable aftertreatment. The upper temperature limit should be not more than 20% above the melting temperature of the polymer, in order that the structure of the coating overall is not endangered. Preferably, the aftertreatment is effected in accordance with the invention at a temperature of about 5% to 15% above the melting temperature of the polymer, especially at a temperature of about 10% above the melting temperature.

In the processes mentioned comprising an aftertreatment by melting, it is advantageous in principle when the applicator described is brought to the corresponding aftertreatment temperature within a minimum period of time in order to avoid cracking in the polymer coating.

According to the invention, the aftertreatment can be effected until all the defects in the polymer coating have been eliminated and the surface thereof has been levelled. Preferred periods of time for such an aftertreatment are less than 1 hour and are preferably less than 30 minutes, especially less than 15 minutes.

Accordingly, a particularly preferred method of the invention is characterized by the following process sequence:
first of all, the uncoated applicator, if required or appropriate, is degreased,
the applicator which has especially been degreased is optionally rinsed with at least one solvent, especially an organic solvent, and then dried,
then a primer layer is optionally applied to the applicator, preferably by electrophoretic deposition,
then a coloring layer is optionally applied, preferably likewise by electrophoretic deposition,
in a subsequent method step, at least one layer of at least one electrically insulating polymer is applied to the optionally precoated applicator, according to the invention by electrophoretic deposition,
for application of a plurality of layers of the electrically insulating polymer, the aforementioned method step can be repeated at least once, in which case the method steps which follow can optionally likewise be repeated after each deposition step,
the polymer coating obtained in this way is optionally treated, especially rinsed, with a solvent,
then the coated applicator is optionally subjected to thermal treatment for drying, preferably at a temperature well below the melting temperature of the electrically insulating polymer, and
then the polymer coating obtained is optionally subjected to thermal aftertreatment by melting this coating.

The invention further encompasses a suspension for the electrophoretic deposition of at least one coating on an applicator for currents, especially HF currents in surgery, especially on a clamp or on a pair of tweezers or on a pair of scissors.

According to the invention, this suspension is characterized in that the suspension comprises at least one electrically insulating polymer in at least one organic solvent.

Preferably, the concentration of the polymer in the suspension is between 10 g/L and 150 g/L, especially between 20 g/L and 100 g/L. The viscosity of the suspension is preferably between 0.1 mPa•s and 10 mPa•s.

With regard to the polymers and organic solvents present in the suspension, reference is made entirely to the corresponding details in connection with the method of the invention. More particularly, the electrically insulating polymer is a polyamide, a polyaryl ether ketone, preferably a polyether ether ketone (PEEK), or a fluoropolymer, preferably a thermoplastic fluoropolymer, especially polytetrafluoroethylene (PTFE) or more particularly polychlorotrifluoroethylene (PCTFE) or ethylene chlorotrifluoroethylene (ECTFE).

The solvent present in the suspension of the invention is preferably an alkane, especially n-hexane and/or n-heptane.

Finally, the invention also encompasses an applicator for currents, especially HF currents in surgery, especially a clamp, pair of tweezers or pair of scissors, having at least one coating of at least one electrically insulating polymer. According to the invention, this applicator is characterized in that the polymer has been applied by electrophoretic deposition from a suspension of the polymer in at least one organic solvent.

The polymer applied to the applicator is preferably a polyamide, a polyaryl ether ketone, preferably a polyether ether ketone (PEEK), or a fluoropolymer, preferably a thermoplastic fluoropolymer, especially polytetrafluoroethylene (PTFE) or more particularly polychlorotrifluoroethylene (PCTFE) or ethylene chlorotrifluoroethylene (ECTFE).

As already elucidated, it is a feature of the coated applicator according to the invention that particular values of breakdown resistance can specifically be provided in the case of particular, especially minimum, layer thicknesses of the polymer coating. The application of coatings of maximum thickness for reasons of safety is unnecessary in the case of the applicators coated in accordance with the invention. Accordingly, it is preferable in the invention when the applicators of the invention provide electrical breakdown resistances between 3 kV/mm and 150 kV/mm, especially between 50 kV/mm and 100 kV/mm, with the abovementioned thicknesses of the polymer coating, preferably between 5 µm and 100 µm, especially between 10 µm and 60 µm.

Further features and advantages of the invention will be apparent from the examples described hereinafter in conjunction with the claims, without the subject matter of the invention being restricted to the examples. At the same time, the features disclosed may each be implemented alone or in combination with one another.

EXAMPLES

For performance of the electrophoretic deposition, a vessel to accommodate the suspension of the electrically insulating polymer to be deposited and a high-voltage source which delivers an output voltage of up to about 4 kV were provided. Also provided was a stirrer for stirring the suspension during the electrophoretic deposition. Finally, a counterelectrode was present, which was connected as the anode during the deposition operation.

Applicators to be coated for HF surgery that were used in the examples were pairs of tweezers for the bipolar technique, called bipolar tweezers. These pairs of tweezers were connected as the cathode during the electrophoretic deposition.

In the pairs of tweezers, the corners were rounded off on all surface regions that were to be provided with the polymer coating, in order in this way to achieve better coating quality with preferably homogeneous layer thickness. In addition, the corresponding surfaces of the pairs of tweezers were blasted with glass beads, in order in this way to provide very fine, clean surfaces for the polymer coating.

The electrically insulating polymer used was the thermoplastic fluoropolymer Halar® ECTFE from Solvay Solexis, specifically the Halar® 6014 product. This is a transparent ethylene chlorotrifluoroethylene copolymer (ECTFE), in which the ethylene and chlorotrifluoroethylene units are in 1:1 alternation in the copolymer. The average particle size of Halar® 6014 is 80 µm (ASTM D 1921-63; Method C). The melting temperature is 225° C.

In addition, variants of the Halar® polymer colored using dry pigments were produced, specifically a blue-colored Halar, a yellow-colored Halar and a black-colored Halar. The blue and black colors were achieved by means of PTFE pigments, the yellow color by means of a nickel titanium yellow dry pigment.

Also used in the examples was a primer, namely the Halar® Primer 6514, which is likewise an ethylene chlorotrifluoroethylene copolymer. This copolymer is a black powder having an average particle size of 80 μm. The melting temperature of this copolymer is likewise 225° C.

The polymers mentioned (transparent ECTFE, colored ECTFE, ECTFE primer) were used to produce suspensions for the electrophoretic deposition using the organic solvent n-heptane. This involved providing both suspensions that contained a dispersant, namely sodium dodecylsulfate (SDS), and those that were free of dispersants.

In all the examples, the procedure was as follows:

First of all, the coated pairs of tweezers were degreased, using an anodic hot degreasing operation. The operating temperature was between 80° C. and 100° C. It was possible for the degreasing to take place either in an alkaline medium (for example sodium hydroxide solution or potassium hydroxide solution) or in an acidic medium (for example phosphoric acid).

Then the pairs of tweezers thus degreased were rinsed with a suitable medium, for example with water (ultrapure water) or alternatively with an alcohol, especially ethanol, or with an alkane, especially n-hexane. This rinsing process was effected at room temperature.

Then the corresponding polymer layers (transparent ECTFE, colored ECTFE and/or ECTFE primer) were applied by electrophoretic deposition, performing electrophoretic deposition with a voltage of 2 kV over a period of 10 seconds in the corresponding experiments. With the corresponding process parameters, it was successively possible to apply either several layers of the same material or layers of different materials one on top of another to the applicator surface.

The concentration of the polymer particles to be deposited in the suspension was 100 g/L.

Then the layers obtained were rinsed with an organic solvent, for example an alcohol, especially ethanol, or an alkane, especially n-hexane. This rinsing operation was generally effected at room temperature.

Then the coatings obtained were dried first at temperatures in the range between 60° C. and 80° C. and subsequently thermally aftertreated with at least partial melting of the polymer. This was effected at an operating temperature between about 250° C. and 270° C.

In the case of electrophoretic deposition of several layers one on top of another, the subsequent steps (rinsing, drying, and melting) were conducted after each deposition step.

According to the examples, with the given process parameters, with single deposition of the electrophoretic coating (2 kV over 10 s), polymer layers with the following thickness were formed:

| | |
|---|---|
| Transparent Halar ® | 80 μm |
| Blue-colored Halar ® | 80 μm |
| Yellow-colored Halar ® | 60 μm |
| Black-colored Halar ® | 40 μm |
| Halar ® primer | 80 μm |

The layer thickness was determined by gravimetric means, by determining the mass of the polymer coating deposited (before and after the electrophoretic deposition). Assuming a homogeneous layer thickness, this mass was used to calculate the corresponding value for this layer thickness.

By multiple execution of the deposition method detailed, coatings with a total layer thickness of about 200 μm were provided. This involved layering either the same polymers one on top of another or different polymers, i.e., for example, a layer sequence of primer beneath layers of transparent or colored ECTFE.

All polymer coatings which were obtained in the examples according to the invention had a breakdown resistance of 5 kV based on the layer thickness of 200 μm. These coatings were stable even under multiple application of a sterilization method in an autoclave, as typically employed in medical technology for the sterilization of bipolar applicators.

The invention claimed is:

1. A method of preparing an applicator for use in electrosurgery, comprising applying at least one coating of at least one electrically insulating polymer to the applicator, resulting in a polymer coating, wherein the applicator is selected from the group consisting of a clamp, a pair of tweezers and a pair of scissors, further wherein the coating is produced partially or entirely by electrophoretic deposition from a suspension of the polymer in at least one organic solvent, wherein the polymer coating has an electrical breakdown resistance of at least 500 V/mm.

2. The method of claim 1, characterized in that the polymer is a transparent polymer.

3. The method of claim 1, characterized in that the polymer is a colored polymer, wherein the polymer is colored by the addition of color pigments.

4. The method of claim 1, characterized in that the polymer is a polyamide or a polyaryl ether ketone.

5. The method of claim 1, characterized in that the polymer is a fluoropolymer.

6. The method of claim 5, characterized in that the fluoropolymer is polytetrafluoroethylene (PTFE) or more particularly polychlorotrifluoroethylene (PCTFE) or ethylene chlorotrifluoro-ethylene (ECTFE).

7. The method of claim 1, characterized in that the polymer coating obtained has a thickness between 5 μm and 500 μm.

8. The method of claim 1, characterized in that the polymer coating has a thickness between 5 μm and 100 μm.

9. The method of claim 1, characterized in that the electrical breakdown resistance is between 3 kV/mm and 150 kV/mm.

10. The method of claim 1, characterized in that the polymer coating is produced at a voltage between 0.2 kV and 4 kV.

11. The method of claim 1, characterized in that the electrophoretic deposition is effected over a period between 5 s and 10 min.

12. The method of claim 1, characterized in that the polymer coating obtained by electrophoretic deposition is subjected to an aftertreatment by melting.

13. The method of claim 12, characterized in that the aftertreatment is effected at a temperature of at maximum 20% above the melting temperature of the polymer.

14. The method of claim 13, characterized in that the aftertreatment is effected over a period of less than 1 hour.

15. A method of preparing an applicator for use in electrosurgery, comprising
(a) degreasing the uncoated applicator, wherein the uncoated applicator is selected from the group consisting of a clamp, a pair of tweezers and a pair of scissors;

(b) rinsing the applicator with a solvent and drying the applicator which has been degreased;
(c) applying a primer layer by electrophoretic deposition;
(d) applying a coloring layer by electrophoretic deposition;
(e) applying at least one electrically insulating polymer to the applicator, resulting in a polymer coating, wherein the coating is produced partially or entirely by electrophoretic deposition from a suspension of the polymer in at least one organic solvent, wherein the polymer coating has an electrical breakdown resistance of at least 500 V/mm;
(f) repeating the preceding steps (c)-(e) electrophoretic application of the polymer coating at least once;
(g) treating the polymer coating obtained with at least one solvent; and
(h) thermally treating the applicator coated with the polymer for drying and optionally for aftertreatment of the polymer coating obtained by melting.

* * * * *